(12) United States Patent
Fukazawa et al.

(10) Patent No.: US 7,557,912 B2
(45) Date of Patent: Jul. 7, 2009

(54) DEFECT INSPECTION APPARATUS AND DEFECT INSPECTION METHOD

(75) Inventors: Kazuhiko Fukazawa, Misato (JP); Takeo Oomori, Sagamihara (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/222,500

(22) Filed: Aug. 11, 2008

(65) Prior Publication Data

US 2008/0316475 A1 Dec. 25, 2008

Related U.S. Application Data

(63) Continuation of application No. 11/473,107, filed on Jun. 23, 2006, now abandoned, which is a continuation of application No. PCT/JP2004/019370, filed on Dec. 24, 2004.

(30) Foreign Application Priority Data

Dec. 26, 2003 (JP) ............................. 2003-434675

(51) Int. Cl.
*G01N 21/88* (2006.01)
(52) U.S. Cl. ................................. 356/237.2; 356/237.5
(58) Field of Classification Search ... 356/237.1–237.5, 356/239.1, 239.7; 250/559.01–559.49
See application file for complete search history.

(56) References Cited

U.S. PATENT DOCUMENTS

| | | | |
|---|---|---|---|
| 6,067,163 A | 5/2000 | Guldi et al. | |
| 6,512,579 B2 | 1/2003 | Oomori et al. | |
| 6,646,735 B2 | 11/2003 | Fukazawa et al. | |
| 6,654,113 B2 | 11/2003 | Fukazawa et al. | |
| 7,118,832 B2 | 10/2006 | Yan | |
| 2001/0015410 A1 | 8/2001 | Imai et al. | |
| 2006/0232769 A1 | 10/2006 | Sugihara et al. | |
| 2008/0094628 A1* | 4/2008 | Fukazawa et al. | ........... 356/369 |

FOREIGN PATENT DOCUMENTS

| | | |
|---|---|---|
| JP | A 62-223613 | 10/1987 |
| JP | A 403249656 | 11/1991 |
| JP | A 09-257719 | 10/1997 |
| JP | A 2001-168159 | 6/2001 |
| JP | A 2002-162367 | 6/2002 |
| WO | WO 2005/064322 A1 | 7/2005 |

\* cited by examiner

*Primary Examiner*—Hoa Q Pham
(74) *Attorney, Agent, or Firm*—Oliff & Berridge, PLC

(57) ABSTRACT

An apparatus and a method for defect inspection enables a reduction in the amount of noise light from an underlying layer and a good defect inspection reliably. The apparatus includes an illumination device that irradiates, with illumination light, a substrate to be inspected including a resist layer having cyclic patterns formed on the upper layer, and an optical image forming system that forms an image of the substrate to be inspected according to light that emerges from the substrate to be inspected by the irradiation with illumination light. The wavelength of the illumination light is set so that intensity of the light from the surface of the resist layer, among the light emerged from the substrate to be inspected, is greater than that of light that has passed through the surface of the cyclic pattern layer formed below the resist layer.

15 Claims, 4 Drawing Sheets

DEFECT INSPECTION APPARATUS AND DEFECT INSPECTION METHOD

CROSS REFERENCE TO RELATED APPLICATION

This is a continuation of application Ser. No. 11/473,107 filed Jun. 23, 2006, which in turn is a continuation of International Application PCT/JP 2004/19370, filed Dec. 24, 2004, designating the U.S., and claims the benefit of priority from Japanese Patent Application No. 2003-434675, filed Dec. 26, 2003, the entire contents of which are incorporated herein by reference.

BACKGROUND OF THE INVENTION

1. Field of the Invention

The present invention relates to a defect inspection apparatus and a defect inspection method for inspecting a defect in a semiconductor wafer or a liquid crystal substrate.

2. Description of the Related Art

In a manufacturing process of semiconductor circuit elements and liquid crystal display elements, a defect inspection is performed for repetitive patterns formed in a resist layer on a surface of a semiconductor wafer or a liquid crystal substrate (generally referred to as a substrate). An automated defect inspection apparatus has a substrate placed on a tiltable stage, irradiates the surface of the substrate with illumination light for inspection, captures an image of the substrate according to the light (for example, primary diffracted light or specular light) that emerges from the repetitive patterns on the substrate, and detects a defect in the repetitive pattern based on brightness information on the image (for example, refer to Japanese Unexamined Patent Application Publication No. 2002-162367). Further, by adjusting the tilt of the stage, it is possible to perform the defect inspection for repetitive patterns having different pitches. Also, it is possible to cope with minute pitches by shortening the wavelength of illumination light.

However, the brightness information of the image captured for defect inspection contains not only defect information of the repetitive patterns formed in the resist layer as the uppermost layer but also information resulting from noise light from the underlying layer. Therefore, in the prior art there are some cases where a large amount of the noise light from the underlying layer prevents a defect inspection with a good S/N ratio (for example, where repetitive patterns are formed in the underlying layer with a pitch which is approximately the same as that of a resist layer, etc.). Note that the noise light from the underlying layer is part of illumination light for inspection that has once passed through the resist layer, reached and reflected from (diffracted by) the underlying layer, and passed through the resist layer again.

SUMMARY OF THE INVENTION

An object of the present invention is to provide a defect inspection apparatus and a defect inspection method which can surely reduce noise light from an underlying layer and perform a good defect inspection.

A defect inspection apparatus of the present invention is provided with an illumination device that irradiates with illumination light a substrate to be inspected including a resist layer having cyclic patterns are formed on an upper layer, and an optical image forming system that forms an image of the substrate to be inspected according to the light that emerges from the substrate to be inspected by the irradiation with the illumination light. Therein, an antireflection layer is formed immediately below the resist layer and the wavelength of the illumination light is set in accordance with information on an absorption wavelength band of the antireflection layer.

Preferably, in the above-mentioned defect inspection apparatus, the information on the absorption wavelength band is an optical absorption spectrum of the antireflection layer.

Preferably, the above-mentioned defect inspection apparatus is also provided with a wavelength band input unit that inputs information on the absorption wavelength band of the antireflection layer and a setting unit that sets a wavelength of the illumination light to a wavelength or a wavelength band included in the absorption wavelength band inputted from the wavelength band input unit.

Preferably, in the above-mentioned defect inspection apparatus, the wavelength of the illumination light is set to an exposure wavelength of exposure equipment which is used to form the cyclic patterns.

Preferably, the above-mentioned defect inspection apparatus is provided with a sensitivity input unit that inputs information on the sensitivity of the resist layer at the wavelength of the illumination light and a control unit that aborts irradiating the substrate to be inspected with the illumination light when a dose of the illumination light reaches its limit dose which is determined in accordance with the sensitivity inputted from the sensitivity input unit.

Further, the defect inspection method of the present invention includes the steps of irradiating with illumination light a substrate to be inspected including a resist layer having cyclic patterns formed on the upper layer; generating an image of the substrate to be inspected by capturing an image according to light that emerges from the substrate to be inspected by the irradiation with the illumination light; and detecting a defect in the cyclic patterns based on brightness information on the image of the substrate to be inspected, in which the wavelength of the illumination light is set in accordance with the optical absorption spectrum of the antireflection layer.

Preferably, the above-mentioned defect inspection method further includes the step of setting the wavelength of the illumination light to an exposure wavelength of the exposure equipment which is used to form the cyclic patterns.

Preferably, the above-mentioned defect inspection method further includes the step of aborting irradiating the substrate to be inspected with the illumination light when a dose of the illumination light reaches its limit dose which is determined in accordance with the sensitivity of the resist layer at the wavelength of the illumination light.

DESCRIPTION OF THE PREFERRED EMBODIMENT

Embodiments of the present invention will be described below in detail using drawings.

First Embodiment

Figure 1:
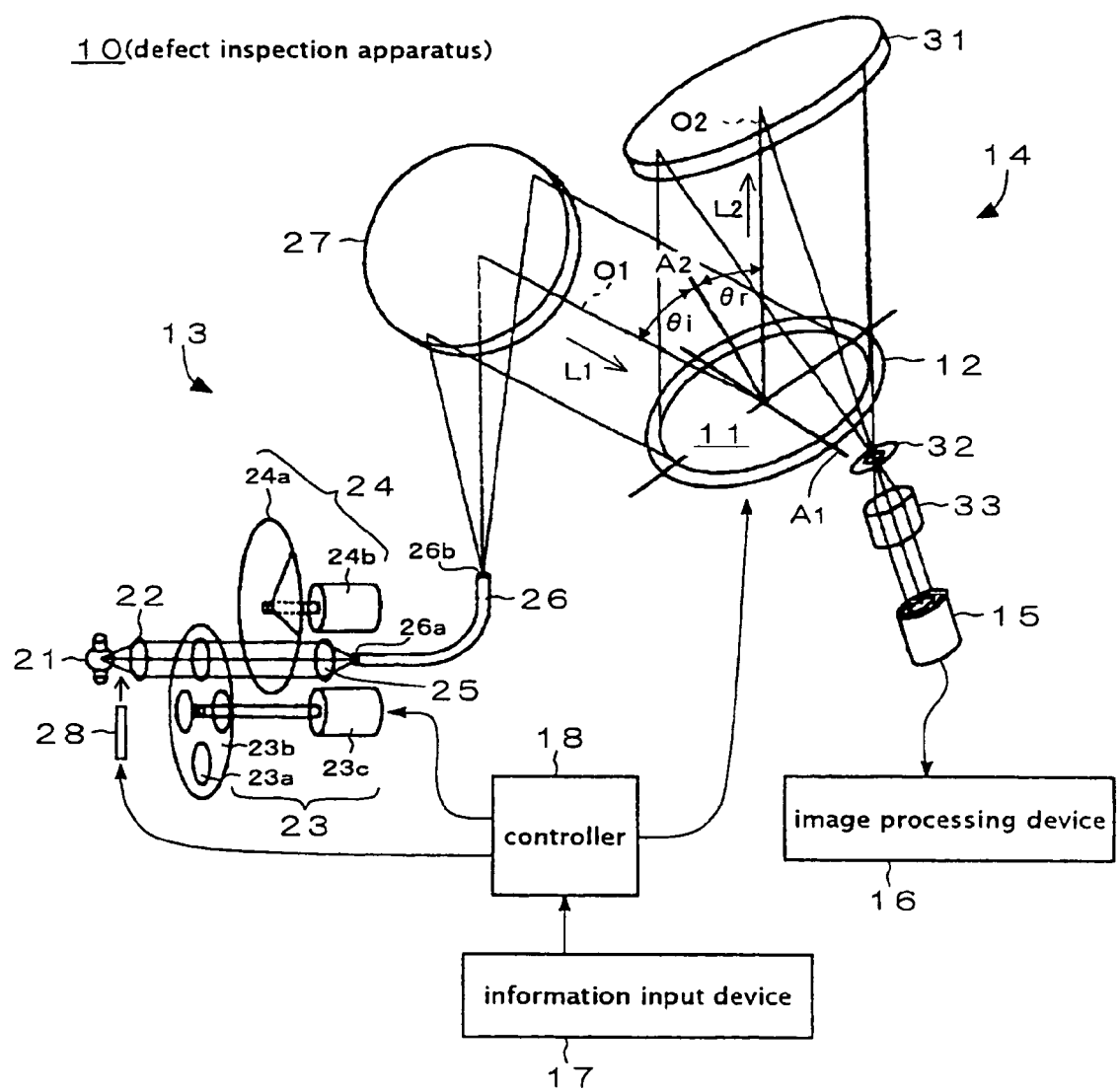
FIG. 1 is a diagram showing an entire configuration of a defect inspection apparatus 10.

As shown in FIG. 1, a defect inspection apparatus 10 in a first embodiment is provided with a stage 12 that supports a semiconductor wafer 11 as a substrate to be inspected, an illumination system 13 that irradiates the semiconductor wafer 11 with illumination light L1, an image forming system 14 that forms an optical image of the semiconductor wafer 11, an image pickup device 15, an image processing device 16, an information input device 17, and a controller 18.

The defect inspection apparatus 10 is an apparatus that automatically performs a defect inspection of repetitive patterns formed in a resist layer on the surface of the semiconductor wafer 11 in the manufacturing process of semiconductor circuit elements, and captures a wafer image for inspection based on diffracted light that emerges from the repetitive patterns. After the resist layer as the uppermost layer is exposed and developed, the semiconductor wafer 11 is conveyed from a not shown wafer cassette or development equipment by a not shown conveying system, and adsorbed by the stage 12.

Figure 3:
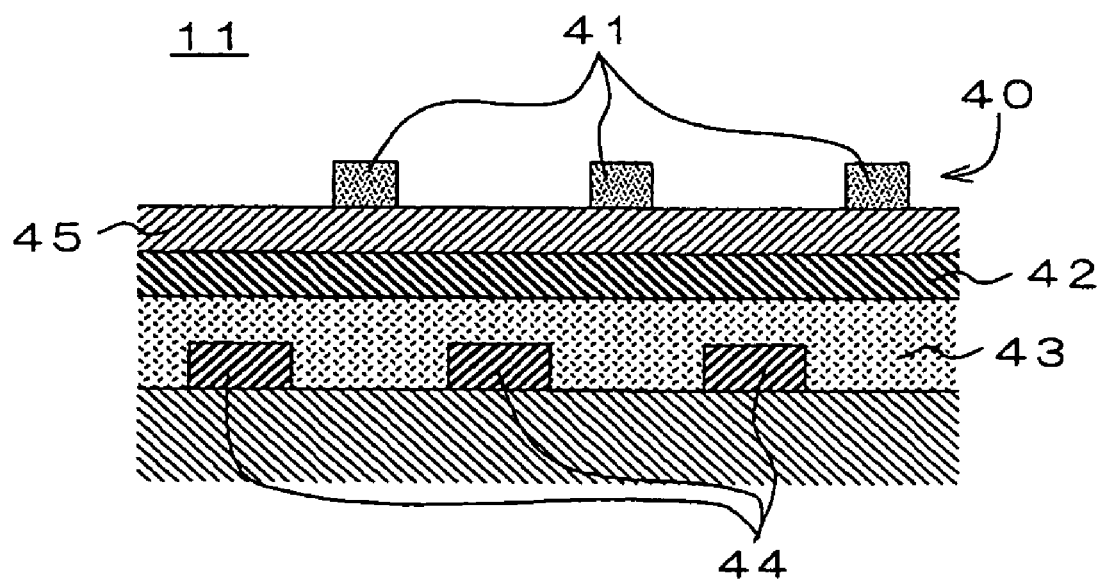
FIG. 3 is a schematic diagram for explaining a cross-sectional configuration of a semiconductor wafer 50.

On the surface of the semiconductor wafer 11, as shown in FIG. 3 (cross section), repetitive patterns 41 (resist patterns) are formed in a resist layer 40 as the uppermost layer. The repetitive patterns 41 are cyclically repeated circuit patterns (cyclic patterns) of a linear arrangement form, and formed through developing processing after the pattern exposure by exposure equipment. Further, on the semiconductor wafer 11, an antireflection layer 45 is formed immediately below the resist layer 40 (the repetitive patterns 41), a layer to be etched 42 is formed immediately below the antireflection layer 45, and repetitive patterns 44 of the underlying layer are formed under the layer to be etched 42 via an insulating layer 43. The antireflection layer 45 is a layer provided to prevent reflection of exposure light during pattern exposure (to reduce light returning to the resist layer 40). By the antireflection layer 45, not less than 99% of the exposure light that has passed through the resist layer 40 is absorbed, therefore, the transfer accuracy of the repetitive patterns 41 during pattern exposure is improved.

The defect inspection apparatus 10 aims to inspect not the repetitive patterns 44 in the underlying layer but the repetitive patterns 41 in the resist layer 40 as the uppermost layer. Therefore, in order to perform a defect inspection with an excellent S/N ratio, it is necessary to reduce the noise light from the repetitive patterns 44 in the underlying layer and efficiently guide diffracted light L2 (FIG. 1) from the repetitive patterns 41 in the resist layer 40 to the image forming system 14 for image formation.

In the first embodiment, information on the wavelength λ of the exposure equipment used to form the repetitive patterns 41 is inputted from the exposure equipment (or the development equipment) to the information input device 17 (FIG. 1) of the defect inspection apparatus 10. Alternatively, the information is registered in advance in an inspection recipe and the information is read out by a not shown reader, and inputted to the information input device 17. The information on the wavelength λ is used in the setting (to be described later) of the wavelength of the illumination light L1 for inspection. Although details will be described later, setting the wavelength of the illumination light L1 to the wavelength λ inputted from the information input device 17 makes it possible to surely reduce the noise light from the underlying layer.

To the information input device 17, information on the sensitivity of the resist layer 40 at the wavelength λ of the exposure equipment is also inputted from the exposure equipment (or the development equipment). Alternatively, the information is registered in advance in the inspection recipe, read out by a reader, not shown, and inputted to the information input device 17. The sensitivity of the resist layer 40 corresponds to the dose [$mJ/cm^2$] at a point of inflection on the graph of a relationship between the exposure dose for the resist layer 40 during pattern exposure and the thickness of the remaining layer after development. Incidentally, a proper exposure dose during pattern exposure is greater than the sensitivity of the resist layer 40. The information on the sensitivity of the resist layer 40 is used for monitoring (to be described later) damage of the resist layer 40 by the illumination light L1 for inspection.

The stage 12 (FIG. 1) is described. The semiconductor wafer 11 is placed on the stage 12 and fixed by, for example, vacuum adsorption. Further, the stage 12 is tiltable within a predetermined range of angle around an axis A1 extending through the surface of the semiconductor wafer 11 by means of a not shown tilt mechanism. The tilt angle of the stage 12 (to be described later) is set by the controller 18. By the tilt adjustment of the stage 12, it is possible to change an angle θi between a normal line A2 of the stage 12 and an optical axis O1 of the illumination system 13 and change an angle θr between a normal line A2 and an optical O2 of the image forming system 14. However, the sum of the angle θi of the illumination system 13 and the angle θr of the image forming system 14 is constant.

The illumination system 13 is described. The illumination system 13 is an eccentric optical system composed of a light source 21, a lens 22, a wavelength selection part 23, a light amount adjusting part 24, a lens 25, a light guide fiber 26, and a concave refection mirror 27. A shutter 28 can be inserted into an illumination light path between the light source 21 and the lens 22. The light source 21 is a discharge light source such as a metal halide lamp or mercury lamp, and emits light in the wavelength range of, for example, 180 nm to 500 nm. The lens 22 converts light from the light source 21 into a parallel light bundle.

The wavelength selection part 23 is provided with four kinds of filter 23a having different transmission wavelength bands and a mechanism (a turret 23b and a motor 23c) for switching between the filters 23a and selects wavelength of light from the lens 22 in accordance with the transmission wavelength range of one of the filters 23a inserted into the illumination light path. In the first embodiment, it is assumed that the transmission wavelength bands of the four kinds of filter 23a are, for example, 436 nm (g-ray), 365 nm (i-ray), 248 nm (corresponding to the oscillation wavelength of a KrF laser), and 193 nm (corresponding to the oscillation wavelength of an ArF laser). These four wavebands are likely to be used for the wavelength λ of the exposure equipment.

The filters 23a (that is, setting of the wavelength of the illumination light L1) in the wavelength selection part 23 is switched by the controller 18 connected to the motor 23c based on the information on the wavelength λ of the exposure equipment inputted from the information input device 17. This processing is described specifically. The controller 18 selects one of the four kinds of wavelength (corresponding to the transmission wavelength range of the filter 23a) that can be set as the wavelength of the illumination light L1, which matches the wavelength λ of the exposure equipment, as a proper wavelength for inspection and outputs a drive signal necessary to insert the filter 23a corresponding to the selected wavelength into the illumination light path to the motor 23c. As a result, the turret 23b rotates according to circumstances and the desired filter 23a (the transmission wavelength range of which nearly matches the wavelength λ of the exposure equipment) is inserted into the illumination light path. In other words, the wavelength of the illumination light L1 is set to the wavelength λ of the exposure equipment.

The light amount adjusting part 24 arranged in the post-stage of the wavelength selection part 23 is provided with a disc-like filter 24a the transmission density (transmittance) of which sequentially changes in the circumferential direction and a mechanism (a motor 24b) that rotates this, and performs light amount adjustment of the light (wavelength λ) from the wavelength selection part 23 in accordance with the rotation angle of the filter 24a. The lens 25 condenses the light (wavelength λ) from the light amount adjusting part 24 at one end 26a of the light guide fiber 26. The light guide fiber 26 transmits the light (wavelength λ) made incident from the one end 26a and emits it from another end 26b toward the concave reflection mirror 27.

The concave reflection mirror 27 is a reflection mirror the reflection surface of which is the inner surface of a sphere and arranged obliquely above the stage 12 so that its front focus substantially matches the other end 26b of the light guide fiber 26 and its rear focus substantially matches the surface of the semiconductor wafer 11. The optical axis O1 of the illumination system 13 after reflection from the concave reflection mirror 27 passes through the center of the stage 12, is inclined by the angle θi with respect to the normal line A2 of the stage 12, and is perpendicular to the axis A1 of the stage 12 (that is, the tilt axis). The illumination system 13 is an optical system telecentric to the semiconductor wafer 11 side.

In the above-mentioned illumination system 13, the light from the light source 21 is used for irradiation of the entire surface of the semiconductor wafer 11 therewith via the optical elements (22 to 27) (illumination light L1). As described already, the wavelength of the illumination light L is set to the wavelength λ, which is the same as that of the exposure equipment. The illumination light L1 is a light bundle of which the direction of the main light beam that reaches an arbitrary point on the surface of the semiconductor wafer 11 is substantially parallel to the optical axis O1. The incidence angle of the illumination light L1 corresponds to the angle θi formed by the optical axis O1 of the illumination system 13 and the normal line A2 of the stage 12.

Then, after the irradiation with the illumination light L1, the diffracted light L2 (for example, primary diffracted light) emerges from the repetitive patterns 41 in the resist layer 40 (FIG. 3) formed on the surface of the semiconductor wafer 11. Further, part of the illumination light L1 passes through the resist layer 40 and reaches the repetitive patterns 44 in the underlying layer, and turns into noise light. However, in the defect inspection apparatus 10 in the first embodiment, the wavelength of the illumination light L1 is set to the wavelength λ, which is the same as that of the exposure equipment, therefore, it is possible to surely reduce the noise light from the repetitive patterns 44 in the underlying layer.

The reason that the noise light can be reduced is described. The wavelength λ of the exposure equipment is a wavelength of exposure light used in pattern exposure for the resist layer 40 (that is, formation of the repetitive patterns 41) and it is matter of course that the wavelength has a high absorptance at the wavelength (optical absorption spectrum) of the antireflection layer 45. Therefore, if the resist layer 40 is irradiated with the illumination light L1 having the wavelength λ, part of the illumination light L1 turns into the diffracted light L2 from the surface of the resist layer 40, however, the rest passes through the resist layer 40 and most (not less than 99%) of it is absorbed within the antireflection layer 45. In other words, it is possible to suppress surely the amount of light that passes through the resist layer 40 and reaches the underlying layer (44) nearly to zero. From this, it is known that the noise light from the underlying layer (44) can be reduced surely if the wavelength of the illumination light L1 is set to the wavelength λ, which is the same as that of the exposure equipment. This means that the intensity of the light from the surface of the resist layer 40 is greater than the intensity of the light that has passed through the surface of the underlying layer (44) formed under the resist layer 40 among the light that emerges from the semiconductor wafer 11.

In other words, by setting the wavelength of the illumination light L1 to the wavelength λ, which is the same as that of the exposure equipment, it is possible to efficiently guide the diffracted light L2 from the repetitive patterns 41 in the resist layer 40 to the image forming system 14. The word "efficiently" means that most of the light guided to the image forming system 14 is the diffracted light L2 and the mixture of the noise light is extremely slight, and therefore, the S/N ratio is high. The direction of the straight line of the repetitive patterns 41 that cause the diffracted light L2 to emerge is substantially parallel to the axis A1 of the stage 12.

The travel direction of the diffracted light L2 changes depending on the wavelength (λ) of the illumination light L1, the incidence angle (θi) of the illumination light L1, and the pitch of the repetitive patterns 41. In order to match the travel direction of the diffracted light L2 with the direction of the optical axis O2 of the image forming system 14, in the defect inspection apparatus 10, tilt adjustment of the stage 12 is performed by the controller 18. For example, it can be thought that a tilt angle of the stage 12 is calculated based on the information on the pitch of the repetitive patterns 41 registered in advance in the inspection recipe and the information on the wavelength (λ) of the illumination light L1, and the tilt angle is set. After the tilt adjustment, the diffracted light L2 travels along the optical axis O2 of the image forming system 14 and its diffraction angle matches the angle θr formed by the normal line A2 of the stage 12 and the optical axis O2 of the image forming system 14.

The intensity of the diffracted light L2 differs between at a defective portion and at a normal portion of the repetitive patterns 41 in the resist layer 40 and also differs depending on the kind of the resist layer 40. Further, the average intensity that occurs from the semiconductor wafer 11 can be adjusted by the irradiation intensity of the illumination light L1. The irradiation intensity of the illumination light L1 can be adjusted in accordance with the rotation angle of the filter 24a of the light amount adjusting part 24 already described above. Because of this, it is possible to secure an optimum amount of light for defect inspection by adjusting the irradiation intensity of the illumination light L1 in accordance with the rotation angle of the filter 24a and by adjusting the average intensity of the diffracted light L2. Such adjustment can be performed based on the information registered in advance in the inspection recipe (for example, the relationship between the kind of the resist layer 40 and the optimum rotation angle of the filter 24a).

In the defect inspection apparatus 10 in the first embodiment, whether or not the semiconductor wafer 11 is irradiated with the illumination light L1 can be switched therebetween by the shutter 28 provided between the light source 21 and the lens 22 of the illumination system 13. The shutter 28 is opened/closed by the controller 18. Normally, the controller 18 retracts the shutter 28 from the illumination light path (open state) when capturing by the image pickup device 15, to be described later, is started and inserts the shutter 28 into the illumination light path (closed state) when capturing is completed.

Further, in the defect inspection apparatus 10 in the first embodiment, the illumination light L1 the wavelength of which is set to the wavelength λ of the exposure equipment is used, therefore, if the dose (irradiation intensity×irradiation time) of the illumination light L1 to the resist layer 40 exceeds a predetermined threshold value (hereinafter, referred to as a limit dose), there is a possibility that the resist layer 40 is damaged and transformed. Therefore, after the shutter 28 is released, the controller 18 monitors occurrence of the damage of the resist layer 40 by the illumination light L1. Then, when the actual dose of the illumination light L1 reaches the limit dose, the shutter 28 is inserted in the illumination light path again (closed state) and irradiation with the illumination light L1 is aborted.

The limit dose of the illumination light L1 is set in accordance with the information on the sensitivity of the resist layer 40 inputted by the information input device 17. The information is on the sensitivity before development and the radiation-resistance of the resist layer 40 after development is improved compared to that before development, therefore, the limit dose of the illumination light L1 may be set to, for example, hundred times that of the sensitivity (before development) of the resist layer 40.

The actual dose of the illumination light L1 is in proportion to the irradiation time when the rotation angle of the filter 24a of the light amount adjusting part 24 is constant and the irradiation intensity of the illumination light L1 is constant. Therefore, it is possible to calculate the irradiation intensity based on the transmission density (transmittance) in accordance with the rotation angle of the filter 24a and to calculate, as a limit time, a time required for the dose to reach the limit dose at this irradiation intensity. In this case, the controller 18 starts to measure the time when the shutter 28 is released and aborts the irradiation with the illumination light L1 when the irradiation time reaches the limit time.

Alternatively, it may also be possible to calculate the actual dose each time based on the irradiation intensity and irradiation time calculated from the rotation angle of the filter 24a and compare the calculated result with the limit dose.

Next, the image forming system 14 is described. The image forming system 14 is an eccentric optical system composed of a concave reflecting mirror 31, an aperture 32, and an image forming lens 33. The optical axis O2 of the image forming system 14 is arranged so as to pass through the center of the stage 12 and incline by the predetermined angle θr with respect to the normal line A2 to the stage 12. The concave reflection mirror 31 is a reflecting mirror like the above-mentioned concave reflection mirror 27 and its front focus substantially coincides with the surface of the semiconductor wafer 11 and its rear focus of the image forming lens 33 substantially coincides with the image pickup plane of the image pickup device 15.

In the above-mentioned image forming system 14, the diffracted light L2 that has emerged from the repetitive patterns 41 in the resist layer 40 (FIG. 2) formed on the surface of the semiconductor wafer 11 is condensed via the concave reflection mirror 31 and the image forming lens 33 after traveling along the optical axis O2 of the concave reflection mirror 31, and reaches the image pickup plane of the image pickup device 15. On the image pickup plane of the image pickup device 15, an optical image of the semiconductor wafer 11 by the diffracted light L2 is formed.

As already described above, in the defect inspection apparatus 10 in the first embodiment, the noise light from the underlying layer (44) of the semiconductor wafer 11 can be reduced surely, therefore, it is possible to obtain a wafer diffracted optical image with a high S/N ratio based on the diffracted light L2 from the repetitive patterns 41 in the resist layer 40 as the uppermost layer. In the wafer diffracted optical image, a contrast occurs caused by the defective portion and the normal portion of the repetitive patterns 41. Further, since the average intensity of the diffracted light L2 is optimum, it is possible to obtain a wafer diffracted optical image with excellent contrast.

The image pickup device 15 is, for example, a CCD image pickup device, and captures a wafer diffracted optical image formed on the image pickup plane, generates a wafer image for inspection, and outputs it to the image processing device 16. The start of capturing by the image pickup device 15 coincides with the release of the shutter 28 of the illumination system 13 (that is, when irradiation with the illumination light L1 starts). At this time, monitoring of the damage to the resist layer 40 by the illumination light L1 is also started. Then, when capturing by the image pickup device 15 is completed without the actual dose of the illumination light L1 reaching the limit dose, a wafer image for inspection is generated.

The image processing device 16 captures the wafer image for inspection from the image pickup device 15 and detects a defect in the repetitive patterns 41 based on the brightness information (contrast) of the wafer image. This detection processing is performed by investigating pattern matching with the image of a conforming wafer (reference image for inspection) stored in advance or the presence/absence of the difference in characteristics from the reference image for inspection stored in advance.

A wafer image for inspection is generated by capturing a wafer diffracted optical image with a high S/N ratio based on the diffracted light L2 from the repetitive patterns 41 in the resist layer 40 as the uppermost layer, therefore, information resulting from the noise light from the underlying layer (44) is hardly included. In other words, it can be thought that the wafer image for inspection includes only information on defects in the repetitive patterns 41 in the resist layer 40 as the uppermost layer. Therefore, it is possible to properly perform a defect inspection without being affected by the underlying layer (44) by processing such a wafer image for inspection. As a result, the inspection accuracy is improved.

Further, in the defect inspection apparatus 10 in the first embodiment, the wavelength of the illumination light L1 is set in accordance with the information on the wavelength λ of the exposure equipment inputted from the information input device 17, therefore, it is possible to cope with a case where the wavelength λ of the exposure equipment is changed according to the kind of the resist layer 40 of the semiconductor wafer 11. In other words, it is possible to always keep the wavelength of the illumination light L1 at a wavelength (the wavelength λ of the exposure equipment) having a high absorptance in the spectral absorption characteristics of the antireflection layer 45 and therefore, to perform a proper defect inspection by suppressing the noise light from the underlying layer (44) substantially to zero.

In the defect inspection apparatus 10 in the first embodiment, the wavelength of the illumination light L1 is set to the wavelength λ, which is the same as that of the exposure equipment, by utilizing the information on the wavelength λ of the exposure equipment, therefore, it is possible to easily realize the above-mentioned proper defect inspection.

Further, in the defect inspection apparatus 10 in the first embodiment, the damage to the resist layer 40 by the illumination light L1 is monitored by utilizing the information on the sensitivity of the resist layer 40 at the wavelength λ of the exposure equipment, and irradiation with the illumination light L1 is aborted when the actual dose of the illumination light L1 reaches its limit dose, therefore, it is possible to keep the damage to the resist layer 40 to a minimum and avoid surely the occurrence of transformation of the resist layer 40.

Second Embodiment

In the above-mentioned first embodiment, the wavelength of the illumination light L1 is set to the wavelength λ, which is the same as that of the exposure light, and then a defect inspection of the repetitive patterns 41 in the resist layer 40 of the semiconductor wafer 11 on which the antireflection layer 45 is formed is performed, however, even in a case where, for example, the antireflection layer is formed on the resist layer 40 and removed in the development process, or the antireflection layer is not formed, it is possible to surely reduce the noise light from the underlying layer (44) of a semiconductor wafer 50 and perform a proper defect inspection, like the above, by using the illumination light with a wavelength having a high absorptance to the resist layer 40.

Figure 2:
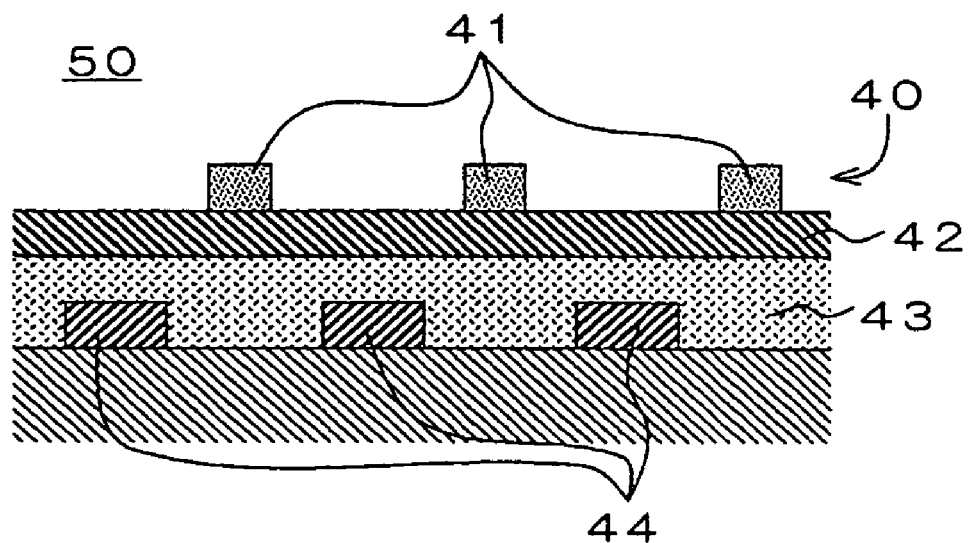
FIG. 2 is a schematic diagram for explaining a cross-sectional configuration of a semiconductor wafer 11.

In FIG. 2, it is assumed that incident light is $I_0$ and the transmittance of the resist layer 40 for light having a wavelength α of the incident light through a total length of t of the portion filled with resist of the light path for to a predetermined incidence angle is Tα (%), then, the intensity $I_2'$ of light that reaches the underlying layer (44) is expressed by the following formula (1). The insulating layer 43 is generally made of quartz and no absorption will occur, therefore, it is not taken into consideration.

$$I_2' = (I_0 - I_1) \times T\alpha/100 \quad (1)$$

The returned light that has been reflected from and diffracted by the underlying layer (44) passes through the resist layer 40 again is expressed by the following formula (2).

$$I_2 = I_2' \times Rm \times T\alpha = (I_0 - I_1) \times (T\alpha/100)^2 \times Rm \quad (2)$$

The ratio of the diffraction efficiency of the resist patterns (41) to that of the underlying layer (44) (the ratio of occurrence of the diffracted light to the incidence light) differs depending on the patterns in the resist layer 40, the reflectivity of the material of the underlying layer (44), and how the respective patterns are formed in the respective layers. For example, when the pitch of the patterns of the resist layer is substantially equal to that of the underlying layer and their pattern density is equal to each other, it is only necessary for the following formula (3) to be satisfied in order to detect diffracted light from the resist layer. In the following formula, Rm is the reflectivity of the underlying layer. If it is assumed that the units of t are nm and the absorption coefficient of the resist is Aα ($cm^{-1}$), then the following formula (4) results.

$$I_1 = I_0 \times Rr > (I_0 - I_1) \times (T\alpha/100)^2 \times Rm \quad (3)$$

$$I_1 = I_0 \times Rr > (I_0 - I_1) \times (1 - A\alpha t \times 10^{-7})^2 \times Rm \quad (4)$$

Therefore, it is only necessary to select the wavelength α that satisfies the above-mentioned formulas (3) and (4) as the wavelength of the illumination light L1.

While the reflectivity of the resist is generally as small as a few %, the underlying layer is made of a metal such as aluminum and copper and its reflectivity is at least about ten times the reflectivity of the resist. For example, when the incident light $I_0$ is 100, the reflectivity for the incident light $I_0$ from the resist pattern is 4%, and the reflectivity of the underlying layer for the incident light is 40%, it can be seen from the formula (3) that if the transmittance Tα is equal to or less than 32% (the absorptance is equal to or greater than 68%), the intensity of the diffracted light from the repetitive patterns is greater than the intensity of the diffracted light from the underlying patterns. Therefore, by selecting the wavelength α that satisfies the condition, it is possible to perform surely a defect inspection of a resist layer even when patterns having the same density and the same pitch are formed in the resist layer and the underlying layer.

Further, for example, when the underlying layer is line-and-space patterns having a predetermined pitch and the resist patterns are hole patterns formed at the same pitch as the predetermined pitch, under the conventional inspection condition, the intensity of the diffracted light from the underlying patterns having a large pattern density is great and in contrast to this, the intensity of the diffracted light from the repetitive patterns having a small pattern density is small, therefore, signals from the resist patterns, which are originally necessary as data, are hidden by the signals of the underlying patterns. Even for such an object to be inspected, by applying the present application, it is possible to properly detect information on the patterns of the resist patterns by suppressing the intensity of the diffracted light from the repetitive patterns to one-tenth or less the intensity of the diffracted light from the underlying layer. In other words, it is only necessary to set the wavelength α so as to satisfy the following conditional formulas (5) and (6).

$$I_1 > (I_0 - I_1) \times 10 \times (T\alpha/100)^2 \times Rm \quad (5)$$

$$I_1 > (I_0 - I_1) \times 10 \times (1 - A\alpha t \times 10^{-7})^2 \times Rm \quad (6)$$

Under the above-mentioned condition, if the transmittance Tα is 10% or less (the absorptance is 90% or greater), it is possible to cope with an inspection of an object to be inspected for which improvement of the S/N ratio is required. Therefore, by setting the wavelength α of the illumination light that satisfies the formula (5), it is possible to perform a proper defect inspection of an object to be inspected, which has a small pattern density of the resist patterns and for which a defect inspection cannot be performed, by selectively obtain information by the diffracted light of the resist patterns.

In both the above-mentioned two examples, a case is described where an object to be inspected is assumed to have the same pitch of the patterns of the resist patterns as that of the underlying patterns and their pattern density being the same or the density of the resist patterns being smaller, and the measurement condition is strict. Therefore, there may be a case where no wavelength exists that satisfies the condition among the absorption characteristics of the resist.

However, an object to be inspected, for which measurement is performed actually, is not limited to this, and there may be a case where the condition is less strict in the pattern density or pattern pitch. Even in such a case, by the conventional method, it is frequent that a sufficient intensity of a signal from a resist layer cannot be obtained because of the decrease in the diffraction efficiency in the repetitive patterns resulting from the difference in the reflectivity between the resist layer and the underlying layer. However, as described in the present embodiment, by using a wavelength having the highest absorptance selectable among the spectral absorption characteristics as an illumination light based on the spectral absorption characteristics of the resist layer 40, it is possible to suppress most the returned light from the underlying layer and it is made possible to perform a defect inspection under a proper condition.

The configuration is described below.

In this case, the spectral absorption characteristics of the resist layer 40 are inputted to the information input device 17 as information on the absorption wavelength band of the resist layer 40. The spectral absorption characteristics correspond to the wavelength dependency of the absorptance (or absorption coefficient, or transmittance) of the resist layer 40. In this specification, a wavelength range in which the absorptance (or absorption coefficient, or transmittance) of the resist layer 40 shows a significant value is referred to as an absorption wavelength band of the resist layer 40. The absorptance of the resist layer 40 is in proportion to the product of the absorption coefficient and the thickness of the resist layer 40. Therefore, it may also be possible to use the absorption coefficient characteristics of the resist layer 40 as information on the absorption wavelength band of the resist layer 40. Further, the information may be only numerical information of the wavelength of the absorption peak specific to the resist layer 40 and the absorption coefficient at the wavelength.

When setting the wavelength of the illumination light L1, the controller 18 compares the absorptance (transmittance) at each wavelength (corresponding to the transmission wavelength region of the filter 23a of the wavelength selection part 23) of the four kinds that can be set as the wavelength of the illumination light L1 among the spectral absorption characteristics of the resist layer 40 inputted from the information input device 17. Then, the wavelength $\alpha$ having the highest absorptance (lowest transmittance) is selected and the wavelength of the illumination light L1 is set to the wavelength $\alpha$. The wavelength $\alpha$ is a wavelength at which absorption is highest among the spectral absorption characteristics of the resist layer 40.

When the wavelength of the illumination light L1 is determined based on the spectral characteristics of the resist layer 40 like the present embodiment, the transmission wavelength region of the filter 23a of the wavelength selection part 23 becomes a wavelength range different from that of the exposure wavelength (generally, the resist is designed so that its transmittance is at least 70% to 80% or greater for the exposure wavelength, therefore, the absorptance for the exposure wavelength is small).

In the present embodiment, wavelengths having significant absorption characteristics among the spectral characteristics of the resist are selected, such as an absorption band specific to a typical compound used as a resist resin such as, for example, polyhydroxy styrene (PHS) and polymethyl methacrylate (PMMA), or as a chemically amplified resist, an absorption band specific to a compound such as a protective group and a solution inhibitor. Further, if the absorption wavelength specific to each resist to be used is already known, it is most preferable that a filter be prepared in advance that is capable of selecting an optimum wavelength in accordance with the spectral characteristics of the resist and the characteristics of the light source.

Figure 5:
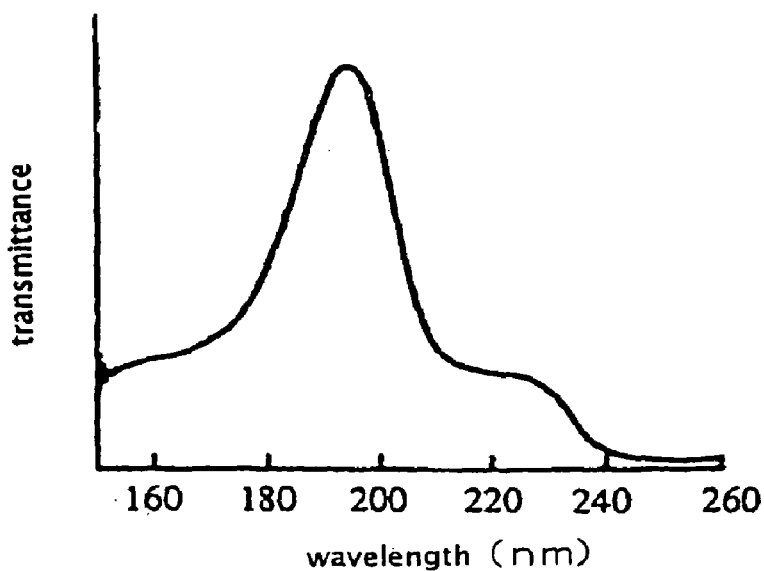
FIG. 5 is a diagram showing an example of an optical absorption spectrum of a polyhydroxy styrene resin (PHS)

FIG. 5 shows a typical absorption wavelength band among the spectral absorption characteristics of a polyhydroxy styrene resin (PHS). The PHS has a large peak in the vicinity of 190 nm to 200 nm. Therefore, in the case of a resist using a PHS resin, if a defect inspection is performed by using a light source including light having a wavelength in the vicinity of 190 nm to 200 nm as light source light and at the same time, using a filter that transmits a wavelength of 190 to 200 nm, it is possible to surely reduce the noise light from the underlying layer. Of course, it is needless to say that if there exists a wavelength range in which absorption is more remarkable, it is possible to select a wavelength of illumination light in accordance with its wavelength, not limited to the absorption band. The spectral characteristics differ depending on the kind of resist, therefore, an optimum wavelength is determined for each resist and an optimum light source and an optimum filter are selected in accordance with the wavelength.

When the resist layer 40 of the semiconductor wafers 11 and 50 is irradiated with the illumination light L1 having the wavelength $\alpha$ in the absorption band specific to the above-mentioned resist layer, part of the illumination light L1 turns into reflected light from or diffracted light L2 by the surface of the resist layer 40 and most of the rest is absorbed within the resist layer 40. In other words, it is possible to suppress surely the amount of light that passes through the resist layer 40 and reaches the underlying layer (44). Further, most of the diffracted light or the scattered light that emerges from the underlying layer (44), which is the light that has reached the underlying layer (44) in small amounts, is absorbed when passing through the resist layer 40 again. Because of this, it is possible to surely reduce the noise light from the underlying layer (44).

As a result, it is possible to efficiently guide the diffracted light L2 from the repetitive patterns 41 in the resist layer 40 as the uppermost layer, to the image forming system 14, obtain a wafer diffracted optical image with a high S/N ratio based on the diffracted light L2, and generate a wafer image for inspection with a high S/N ratio that hardly includes information resulting from the noise light from the underlying layer (44). In other words, it can be thought that the wafer image for inspection includes only information on defects in the repetitive patterns 41 in the resist layer 40 as the uppermost layer. Therefore, it is possible to properly perform a defect inspection of the semiconductor wafers 11 and 50 by processing such a wafer image for inspection. As a result, the inspection accuracy is improved.

Further, in the second embodiment, the wavelength of the illumination light L1 is set in accordance with the spectral absorption characteristics of the resist layer 40 (information on the absorption wavelength band of the resist layer 40) inputted from the information input device 17, therefore, it is possible to cope with the change of the kind of the resist layer 40 of the semiconductor wafers 11 and 50. In other words, even if any resist material is used for the resist layer 40, it is possible to set the wavelength of the illumination light L1 always to the wavelength $\alpha$ having a high absorptance in the spectral absorption characteristics of the resist layer 40 by selecting the wavelength $\alpha$ of the illumination light L1 that is considerably absorbed by the resist layer 40, and therefore, it is possible to perform a proper defect inspection by reducing surely the noise light from the underlying layer (44).

The second embodiment is effective when a semiconductor wafer on which an antireflection layer is not formed is inspected. In other words, by setting the wavelength of the illumination light L1 to the above-mentioned wavelength $\alpha$, the amount of light absorbed within the resist layer 40 can be increased and the noise light from the underlying layer 44 can be reduced. Because of this, it is possible to perform a defect inspection with a proper S/N ratio. Further, in the present embodiment, the illumination light L1 the wavelength of which is other than the wavelength of the exposure light is used, therefore, although the illumination light L1 is absorbed by the resist layer 40, it is possible to prevent the light from contributing to an optical reaction (a solubilization reaction or an insolubilization reaction in the development liquid) or to suppress its degree of contribution. In other words, an inspection is performed using a wavelength having no sensitivity to the resist layer 40 or having a low sensitivity compared to that of the exposure light, therefore, it is possible to suppress the transformation of the resist 40 to a small degree.

Third Embodiment

In the above-mentioned second embodiment, the wavelength of the illumination light L1 is set in accordance with the spectral absorption characteristics of the resist layer 40 (information on the absorption wavelength band of the resist layer 40), however, like the first embodiment, when the antireflection layer 45 is sandwiched between the resist layer 40 and the underlying layer 44 like the semiconductor wafer 50 shown in FIG. 3, if the wavelength of the illumination light L1 is included in the absorption wavelength band of the antireflection layer 45 (even if not included in the absorption wavelength band of the resist layer 40 or not the wavelength λ, which is the same as that of the exposure equipment), it is possible to surely reduce the noise light from the underlying layer (44) of the semiconductor wafer 50 and perform a proper defect inspection in the same manner described above.

Figure 6:
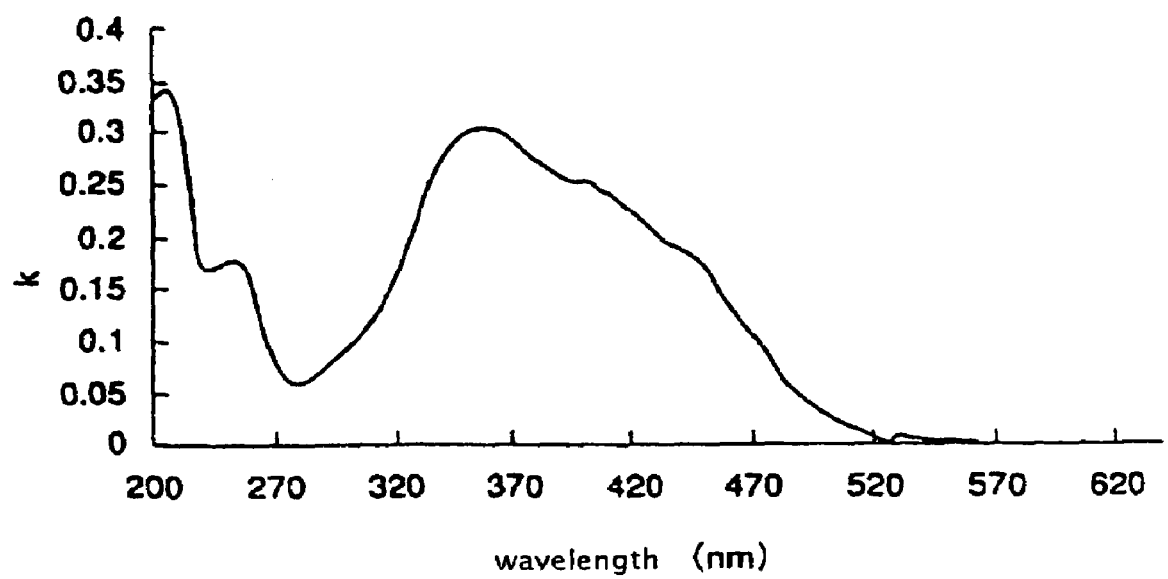
FIG. 6 is a diagram showing an example of spectral absorption coefficient characteristics of an antireflection layer.

FIG. 6 shows an example of the spectral absorption coefficient characteristics of an antireflection layer (the source of FIG. 6: Clariant (Japan) K.K. catalogue P29 AZ BARLi-II series, for manufacturing VLSI, bottom application type antireflection layer, in conformance with i-ray).

The antireflection layer is an antireflection layer for exposure with the i-ray (365 nm), therefore, the spectral absorption coefficient characteristics have its peak at 365 nm, however, a large mountain-shaped band of absorption is further formed by a plurality of absorption bands overlapped on each other in the range from 320 nm to 470 nm. Further, there exist absorption bands having their peaks at about 200 nm and about 240 nm. Therefore, even if a wavelength other than that of 365 nm is used as illumination light, it is possible to suppress the noise light from the underlying layer to a sufficiently small value by using an arbitrary wavelength β in the absorption band described above.

In FIG. 3, if it is assumed that the transmittance of the antireflection layer 45 for the wavelength α of incident light through an optical path ta in the antireflection layer in accordance with the incidence angle of the incident light is Tβ (%), then, the intensity $I_2'$ of the light that reaches the underlying layer (44) is expressed by the following formula (7). The absorption of the resist layer and of the insulating layer 43 is not taken into consideration.

$$I_2'=(I_0-I_1)\times T\beta/100 \tag{7}$$

The returned light that has been reflected from and diffracted by the underlying layer (44) passes through the resist layer 40 again is expressed by the following formula (8).

$$I_2=I_2'\times Rm\times T\beta=(I_0-I_1)\times(T\beta/100)^2\times Rm \tag{8}$$

The ratio of the diffraction efficiency of the resist patterns to that of the underlying layer (the ratio of occurrence of the diffracted light to the incidence light) differs depending on the patterns in the resist layer, the reflectivity of the material of the underlying layer, and how the respective patterns are formed in the respective layers. For example, when the pitch of the patterns of the resist layer is substantially equal to that of the underlying layer and their pattern density is equal to each other, it is only necessary for the following formula (9) to be satisfied in order to detect diffracted light from the resist layer. If it is assumed that the units of ta are nm and the absorption coefficient of the resist is Aβ (cm$^{-1}$), then the following formula (10) results.

$$I_1=I_0\times Rr>(I_0-I_1)\times(T\beta/100)^2\times Rm \tag{9}$$

$$I_1=I_0\times Rr>(I_0-I_1)\times(1-A\beta t\times 10^{-7})^2\times Rm \tag{10}$$

Therefore, it is only necessary to select the wavelength α that satisfies the above-mentioned formulas (9) and (10) as the wavelength of the illumination light L1.

Further, like the second embodiment, when the underlying layer is line-and-space patterns having a predetermined pitch and the resist patterns are hole patterns formed at the same pitch as the predetermined pitch, the following formulas (11) and (12) are obtained.

$$I_1>(I_0-I_1)\times 10\times(T\beta/100)^2\times Rm \tag{11}$$

$$I_1>(I_0-I_1)\times 10\times(1-A\beta ta\times 10^{-7})^2\times Rm \tag{12}$$

In this case, the spectral absorption characteristics of the antireflection layer 45 are inputted to the information input device 17 as information on the absorption wavelength band of the antireflection layer 45. The spectral absorption characteristics correspond to the wavelength dependency of the absorptance (or absorption coefficient, or transmittance) of the antireflection layer 45. In this specification, a wavelength range in which the absorptance (or absorption coefficient, or transmittance) of the antireflection layer 45 shows a significant value is referred to as an absorption wavelength band of the antireflection layer 45. The absorptance of the antireflection layer 45 is in proportion to the product of the absorption coefficient and the thickness of the antireflection layer 45.

When setting the wavelength of the illumination light L1, the controller 18 compares the absorptance (transmittance) at each wavelength (corresponding to the transmission wavelength region of the filter 23a of the wavelength selection part 23) of the four kinds that can be set as the wavelength of the illumination light L1 among the spectral absorption characteristics of the antireflection layer 45 inputted from the information input device 17. Then, the wavelength β having the highest absorptance (lowest transmittance) is selected and the wavelength of the illumination light L1 is set to the wavelength β. The wavelength β in this case is included in the absorption wavelength region of the antireflection layer 45 and is a wavelength having a comparatively high absorptance (low transmittance) in the spectral absorption characteristics of the antireflection layer 45. In other words, it is a wavelength having the highest absorptance.

Therefore, if the resist layer 40 of the semiconductor wafers 50 is irradiated with the illumination light L1 having the wavelength β, part of the illumination light L1 turns into diffracted light L2 and most of the rest is absorbed within the antireflection layer 45. In other words, it is possible to suppress surely the amount of light that passes through the antireflection layer 45 and reaches the underlying layer (44). Further, most of the diffracted light or the scattered light that emerges from the underlying layer (44), which is the light that has reached the underlying layer (44) in small amounts, is absorbed when passing through the antireflection layer 45 again. Because of this, it is possible to surely reduce the noise light from the underlying layer (44).

As a result, it is possible to efficiently guide the diffracted light L2 from the repetitive patterns 41 in the resist layer 40 as the uppermost layer, to the image forming system 14, obtain a wafer diffracted optical image with a high S/N ratio based on the diffracted light L2, and generate a wafer image for inspection with a high S/N ratio that hardly includes information resulting from the noise light from the underlying layer (44). In other words, the wafer image for inspection includes only information on defects in the repetitive patterns 41 in the resist layer 40 as the uppermost layer. Therefore, it is possible to properly perform a defect inspection of the semiconductor wafers 50 by processing such a wafer image for inspection. As a result, the inspection accuracy is improved.

Further, in the third embodiment, the wavelength of the illumination light L1 is set in accordance with the spectral absorption characteristics of the antireflection layer 45 (information on the absorption wavelength band of the antireflection layer 45) inputted from the information input device 17, therefore, it is possible to cope with the change of the kind of the antireflection layer 45 of the semiconductor wafer 50. In other words, even if any antireflection layer material is used for the antireflection layer 45, it is possible to set the wavelength of the illumination light L1 always to the wavelength β having a high absorptance in the spectral absorption characteristics of the antireflection layer 45 by selecting the wavelength β of the illumination light L1 that is considerably absorbed by the antireflection layer 45 depending on the data of the spectral characteristics specific to the antireflection layer, and therefore, it is possible to perform a proper defect inspection by reducing surely the noise light from the underlying layer (44).

Such a third embodiment is effective when the absorption at the selected wavelength β among the spectral absorption characteristics of the antireflection layer 45 is greater in degree than the absorption at the wavelength λ of the exposure equipment. In other words, by setting the wavelength of the illumination light L1 to the above-mentioned wavelength β, the amount of light absorbed within the antireflection layer 45 can be increased and the noise light from the underlying layer (44) can be further reduced. Because of this, it is possible to perform a defect inspection with a proper S/N ratio. Further, wavelengths other than that of the exposure light can be used as illumination light also in the present embodiment, therefore, the present embodiment is effective, like the second embodiment, when it is desired to suppress the transformation of the resist layer 40 to a smaller level than when the wavelength of the exposure equipment is used.

Fourth Embodiment

Here, a case is described where both the spectral absorption characteristics of the resist layer 40 and the spectral absorption characteristics of the antireflection layer 45 are inputted to the information input device 17 in a defect inspection of the semiconductor wafer 50 (FIG. 3) having the antireflection layer 45.

In FIG. 3, without the absorption of the resist layer and of the antireflection layer taken into consideration, the intensity $I_2'$ of the light that reaches the underlying layer is expressed by the following formula (13). The absorption of the insulating layer 43 is not taken into consideration.

$$I_2' = (I_0 - I_1) \times T\alpha/100 \times T\beta/100 \quad (13)$$

Further, the returned light having been reflected from and diffracted by the underlying layer (44) and having passed through the resist layer 40 again is expressed by the following formula (14).

$$I_2 = I_2' \times Rm \times T\alpha/100 \times T\beta/100 = (I_0 - I_1) \times (T\alpha \cdot T\beta/10000)^2 \times Rm \quad (14)$$

The ratio of the diffraction efficiency of the resist patterns to that of the underlying layer (the ratio of occurrence of the diffracted light to the incidence light) differs depending on the patterns in the resist layer, the reflectivity of the material of the underlying layer, and how the respective patterns are formed in the respective layers. For example, when the pitch of the patterns of the resist layer is substantially equal to that of the underlying layer and their pattern density is equal to each other, it is only necessary for the following formula (15) to be satisfied in order to detect diffracted light from the resist layer. In the following formula, Rm is the reflectivity of the underlying layer. If it is assumed that the units of t are nm and the absorption coefficient of the resist is Aβ (cm$^{-1}$), then resulting in the following formula (16).

$$I_1 = I_0 \times Rr > (I_0 - I_1) \times (T\alpha \cdot T\beta/10000)^2 \times Rm \quad (15)$$

$$I_1 = I_0 \times Rr > (I_0 - I_1) \times (1 - A\alpha t \times 10^{-7})^2 \times (1 - A\beta t a \times 10^{-7})^2 \times Rm \quad (16)$$

Therefore, it is only necessary to select the wavelength α that satisfies the above-mentioned formulas (15) and (16) as the wavelength of the illumination light L1.

Further, like the second embodiment, when the underlying layer is line-and-space patterns having a predetermined pitch and the resist patterns are hole patterns formed at the same pitch as the predetermined pitch, it is possible to selectively take out only the diffracted light from the resist patterns by setting the wavelength γ of the illumination light L1 that satisfies the following formulas.

$$I_1 > (I_0 - I_1) \times 10 \times (T\alpha \cdot T\beta/10000)^2 \times Rm \quad (17)$$

$$I_1 > (I_0 - I_1) \times 10 \times (1 - A\alpha t \times 10^{-7})^2 \times (1 - A\beta t a \times 10^{-7})^2 \times Rm \quad (18)$$

When setting the wavelength of the illumination light L1, the controller 18 finds the total spectral absorption characteristics of the spectral absorption characteristics of the resist layer 40 the thickness of which is already known inputted from the information input device 17 and the spectral absorption characteristics of the antireflection layer 45 the thickness of which is already known, and compares the absorptance (transmittance) at each wavelength (corresponding to the transmission wavelength region of the filter 23a of the wavelength selection part 23) of the four kinds that can be set as the wavelength of the illumination light L1 among the total spectral absorption characteristics. Then, the wavelength γ having the highest absorptance (lowest transmittance) is selected and the wavelength of the illumination light L1 is set to the wavelength γ. The wavelength γ in this case is included in at least one of the absorption wavelength region of the resist layer 40 and the absorption wavelength region of the antireflection layer 45 and is a wavelength having a comparatively high absorptance (low transmittance) in the total spectral absorption characteristics. In other words, it is a wavelength having the highest absorptance.

Therefore, by irradiating the resist layer 40 of the semiconductor wafer 50 with the illumination light L1 having the wavelength of γ, it is possible to surely reduce the nose light from the underlying layer (44). As a result, it is possible to generate a wafer image for inspection with a high S/N ratio that hardly includes information resulting from the noise light from the underlying layer (44), that is, to generate a wafer image for inspection that includes only information on defects in the repetitive patterns 41 in the resist layer 40. Therefore, it is possible to properly perform a defect inspection of the repetitive patterns 41 of the semiconductor wafer 50 and the inspection accuracy is improved.

Further, in the fourth embodiment, the wavelength of the illumination light L1 is set in accordance with the spectral absorption characteristics of the resist layer 40 and the spectral absorption characteristics of the antireflection layer 45 inputted from the information input device 17, therefore, it is possible to cope with the change of the kinds of the resist layer 40 and the antireflection layer 45 of the semiconductor wafer 50. In other words, even if any material is used for the resist layer 40 and the antireflection layer 45, it is possible to set the wavelength of the illumination light L1 always to the wavelength γ having a high absorptance in the total spectral absorption characteristics by selecting the wavelength γ of the illumination light L1 that is considerably absorbed by both or either of them in accordance with the data of both the spectral characteristics of the resist layer and the antireflection layer, therefore, it is possible to perform a proper defect inspection by reducing surely the noise light from the underlying layer (44).

The fourth embodiment is effective when the absorption at the selected wavelength γ among the total spectral absorption characteristics of the resist layer 40 and the antireflection layer 45 is greater in degree than the absorption at the wavelength λ of the exposure equipment and greater in degree than the absorption at the wavelengths α and β selected in the second and third embodiments. In other words, by setting the wavelength of the illumination light L1 to the above-mentioned wavelength γ, the amount of light absorbed within the resist layer 40 or the antireflection layer 45 can be increased and the noise light from the underlying layer (44) can be further reduced. Because of this, it is possible to perform a defect inspection with a proper S/N ratio.

In the second to fourth embodiments described above, at least one of the spectral absorption characteristics of the resist layer 40 and the spectral absorption characteristics of the antireflection layer 45 is inputted to the defect inspection apparatus 10, however, the present invention is not limited to this. It is more preferable that, in addition to the spectral absorption characteristics, the spectral sensitivity characteristics of the resist layer (the wavelength dependency of the resist sensitivity) be inputted and at the same time, a wavelength (α', β', γ') of the illumination light L1 having a high absorptance for the resist layer or the antireflection layer, or for both, and having a low sensitivity to the resist layer be inputted. Further, it may also be possible to use the absorption coefficient characteristics of the resist layer 40 as information on the absorption wavelength band of the resist layer 40 as described above. In this case, if information on the layer thickness is inputted further, it is possible to calculate the absorptance (transmittance) with precision and properly select the wavelength α of the illumination light L1 in accordance with the calculated absorptance.

Further, when the kind of the resist (or the antireflection layer, or both) to be used and the optimum wavelength (λ, α, β, γ, α', β', γ') selected by the above-mentioned method in accordance with the resist (or the antireflection layer, or both) are already known, it is possible to obtain the same effect also by inputting information on the kind of the resist layer 40 or the antireflection layer 45 as identification information. Identification information includes the type name of the resist layer or the antireflection layer, the name of the manufacturing process (critical process, rough process, implantation process, etc.) in which these layers are used, symbols such as A, B, and C, etc.

In this case, it is only necessary to make it possible to select the optimum wavelength for the four kinds of wavelength (corresponding to the transmission wavelength region of the filter 23a of the wavelength selection part 23) that can be set as the wavelength of the illumination light L1 and select an arbitrary one included in the absorption wavelength band inputted from the information input device 17, the resist corresponding to the identification information, or the absorption wavelength band of the antireflection layer and set it to this wavelength.

In the above-mentioned first to fourth embodiments, an example of the defect inspection apparatus 10 is described, in which the wavelength of the illumination light L1 is switched to any one of the four kinds of discrete wavelength (corresponding to the transmission wavelength region of the filter 23a of the wavelength selection part 23), however, the present invention is not limited to this. The present invention can also be applied to a case where the wavelength of the illumination light L1 is varied continuously. In this case, it is possible to set the wavelength of the illumination light L1 to a wavelength (peak wavelength) having the highest absorptance (absorption coefficient) among the spectral absorption characteristics (or the absorption coefficient characteristics) inputted from the information input device 17. When the spectral absorption characteristics (the absorption coefficient characteristics) of the antireflection layer 45 are inputted, it is possible to set to a wavelength having the highest absorptance (or the absorption coefficient or the transmittance) among the spectral characteristics (absorption characteristics) of the antireflection layer 45. When the spectral absorption characteristics (the absorption coefficient characteristics) of both the resist layer 40 and the antireflection layer 45 are inputted, it is possible to set to a wavelength having the highest absorptance (or the absorption coefficient or the transmittance) among the total spectral absorption characteristics (the absorption coefficient characteristics). In either case, if the spectral absorption characteristics of the resist layer 40 are further inputted, it is possible to set to a wavelength having a high absorptance of the resist layer 40 and a low sensitivity.

Fifth Embodiment

Figure 4:
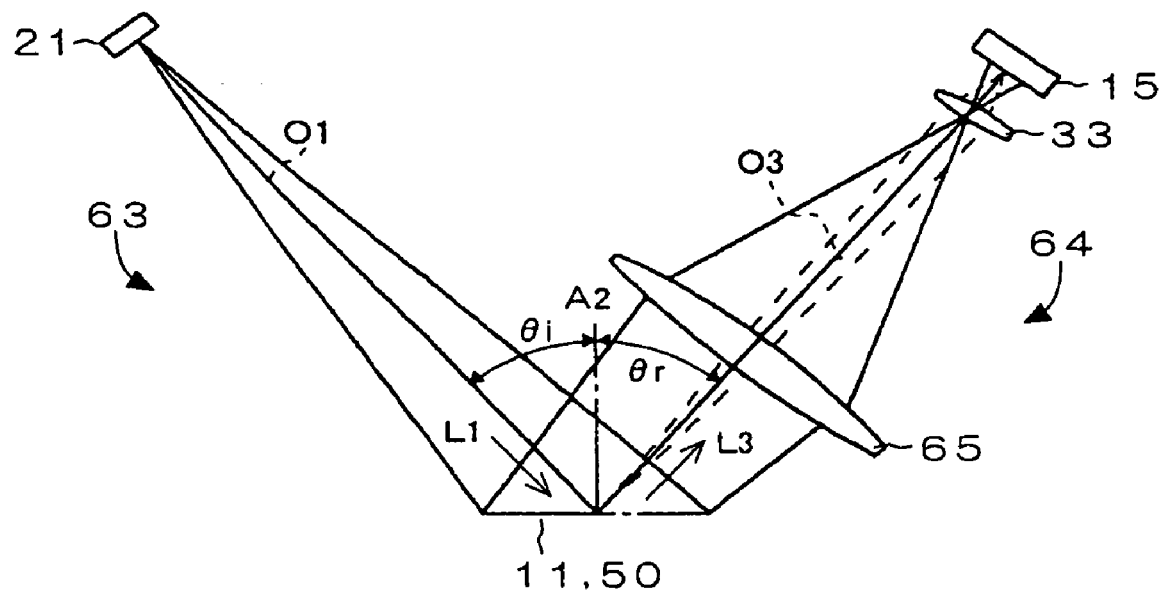
FIG. 4 is a diagram showing a configuration of a defect inspection apparatus 60.

Here, an example is described where a wafer image for inspection is captured based on the specular light that emerges from the repetitive patterns 41 of the resist layer 40 of the semiconductor wafers 11 and 50. In a defect inspection apparatus 60 in the fifth embodiment, as shown in FIG. 4, an illumination system 63 and an image forming system 64 are provided instead of the illumination system 13 and the image forming system 14 in FIG. 1. The illumination system 63 is provided with a shutter, not shown, a wavelength selection part, and a light amount adjusting part on an illumination light path, in addition to the light source 21, which is the same as that in FIG. 1. The wavelength selection part changes the wavelength of the illumination light L1 discretely or continuously. The shutter and the light amount adjusting part are the same as the shutter 28 and the light amount adjusting part 24 in FIG. 1. The image forming system 64 is provided with a light condensing lens 65 that performs a function similar to that of the concave reflection mirror 31 in FIG. 1 and the image forming lens 33 similar to that in FIG. 1. Further, although not shown schematically, the defect inspection apparatus 60 is also provided with the stage 12, the image processing device 16, the information input device 17, and the controller 18 like FIG. 1.

In the defect inspection apparatus 60, the resist layer 40 of the semiconductor wafers 11 and 50 is irradiated with the same illumination light L1 as those described above (for example, any one of the wavelengths λ, α, β, γ, α', β', γ'). Because of this, it is possible to surely reduce the noise light from the underlying layer (44). Further, the angle θi of the illumination system 63 and the angle θr of the image forming system 64 are set (θi=θr) so that specular light L3 that emerges from the repetitive patterns 41 is guided along an optical axis O3 of the image forming system 64. The specular light L3 is zero-order diffracted light and diffracted light of other orders (for example, above-mentioned diffracted light L2 etc.) travels in directions deviated from the optical axis O3 of the image forming system 64.

Therefore, it is possible to efficiently guide the specular light L3 from the repetitive patterns 41 in the resist layer 40 as the uppermost layer, to the image forming system 64, obtain a wafer diffracted optical image with a high S/N ratio based on the specular light L3, and generate a wafer image for inspection with a high S/N ratio that hardly includes information resulting from the specular light L3. In other words, it can be thought that the wafer image for inspection includes only information on defects in the repetitive patterns 41 in the resist layer 40 as the uppermost layer. Therefore, it is possible to properly perform a defect inspection of the semiconductor wafers 11 and 50 by processing such a wafer image for inspection. As a result, the inspection accuracy is improved.

Modifications

In the above-mentioned embodiments, the illumination systems 13 and 63 are provided with the discharge light source (21) and the wavelength selection part (23), however, the present invention is not limited to this. Instead of providing the discharge light source and the wavelength selection part, it may also be possible to provide, for example, a KrF excimer laser (oscillation wavelength: 248 nm), an ArF excimer laser (oscillation wavelength: 193 nm), a $F_2$ laser (oscillation wavelength: 165 nm), etc., and make it possible to switch the lasers in accordance with an illumination wavelength. Further, an example of a defect inspection apparatus in which the illumination wavelength can be changed is described, however, the present invention can be applied even to a case where the illumination wavelength is fixed. Furthermore, it may also be possible to omit the light guide fiber 26 of the defect inspection apparatus 10. During capturing by the image pickup device 15, it may also be possible to change the setting of the light amount adjusting part 24 and adjust the irradiation intensity. Further, the present invention can be applied to a case where, different from the defect inspection apparatus 10, an illumination system and an image forming system are movable with respect to a fixed stage.

Furthermore, in the above-mentioned embodiments, the semiconductor wafer 11 is treated as a substrate to be inspected, however, the present invention is not limited to this. The present invention can also be applied to a case where a defect inspection of a liquid crystal substrate (substrate to be inspected) is performed in the manufacturing process of liquid crystal display elements. Not limited to a case where defect detection processing is performed by the image processing device 16 of the defect inspection apparatus, it is also possible to obtain the same effect in a case where an external computer connected to the defect inspection apparatus is used.

The invention is not limited to the above embodiments and various modifications may be made without departing from the spirit and scope of the invention. Any improvement may be made in part or all of the components.

What is claimed is:

1. A defect inspection apparatus comprising:
    an illumination optical system that irradiates a resist layer with illumination light, the resist layer is a top layer of a substrate to be inspected and has repetitive patterns; and
    an optical image forming system that forms an optical image according to diffracted light of a single intended diffraction order or specular light, among the light that emerged from the repetitive patterns of the resist layer; and
    a processing unit that detects a defect in the repetitive patterns based on intensity information of the optical image, wherein:
    a wavelength of the illumination light is set so that intensity of the light involved in formation of the optical image, among the light that emerged from the repetitive patterns of the resist layer, is greater than intensity of light that has mixed, in the optical image forming system, among the light that emerged from the repetitive patterns formed below the resist layer.

2. The defect inspection apparatus according to claim 1, wherein a wavelength of the illumination light is set in accordance with information on an absorption wavelength band of the resist layer.

3. The defect inspection apparatus according to claim 2, wherein the information on the absorption wavelength band of the resist layer is an optical absorption spectrum of the resist layer.

4. The defect inspection apparatus according to claim 2, further comprising:
    a wavelength band input unit that inputs the information on the absorption wavelength band of the resist layer; and
    a setting unit that sets the wavelength of the illumination light to a wavelength or a wavelength band included in the absorption wavelength band inputted from the wavelength band input unit.

5. The defect inspection apparatus according to claim 1, wherein an antireflection layer is formed immediately below the resist layer; and
    the wavelength of the illumination light is set in accordance with at least one of an information on an absorption wavelength band of the resist layer and an information on an absorption wavelength band of the antireflection layer.

6. The defect inspection apparatus according to claim 5, wherein the information on the absorption wavelength band is at least one of an optical absorption spectrum of the antireflection layer and an optical absorption spectrum of the resist layer.

7. The defect inspection apparatus according to claim 5, further comprising:
    a wavelength band input unit that inputs at least one of the information on an absorption wavelength band of the resist layer and the information on an absorption wavelength band of the antireflection layer; and
    a setting unit that sets the wavelength of the illumination light to a wavelength or a wavelength band included in the absorption wavelength band inputted from the wavelength band input unit.

8. The defect inspection apparatus according to claim 1, wherein the wavelength of the illumination light is set to an exposure wavelength of exposure equipment which is used to form the repetitive patterns.

9. The defect inspection apparatus according to claim 1, further comprising:
    a sensitivity input unit that inputs information on sensitivity of the resist layer at the wavelength of the illumination light; and
    a controller unit that aborts irradiating the substrate to be inspected with the illumination light when a dose of the illumination light reaches a limit dose which is determined in accordance with the sensitivity inputted from the sensitivity input unit.

10. A defect inspection method comprising the steps of:
    irradiating a resist layer with illumination light formed by an illumination optical system, the resist layer is a top layer of a substrate to be inspected and has repetitive patterns;
    capturing an image of an optical image formed by an optical image forming system according to diffracted light of a single intended diffraction order or specular light, among the light that emerged from the repetitive patterns of the resist layer; and detecting a defect in the repetitive patterns based on intensity information of the captured image, wherein a wavelength of the illumination light is set so that intensity of the light involved in formation of the optical image, among the light that emerged from the repetitive patterns of the resist layer, is greater than intensity of light that has mixed, in the optical image forming system, among the light that emerged from repetitive patterns formed below the resist layer.

11. The defect inspection method according to claim 10, wherein a wavelength of the illumination light is set in accordance with an optical absorption spectrum of the resist layer.

12. The defect inspection method according to claim 10, wherein an antireflection layer is formed immediately below the resist layer; and a wavelength of the illumination light is set in accordance with at least one of an optical absorption spectrum of the resist layer and an optical absorption spectrum of the antireflection layer.

13. The defect inspection method according to claim 10, wherein the wavelength of the illumination light is set to an exposure wavelength of an exposure equipment used to form the repetitive patterns.

14. The defect inspection method according to claim 10, wherein the irradiation with the illumination light is aborted when the dose of the illumination light for the substrate to be inspected reaches a limit dose which is determined in accordance with a sensitivity of the resist layer at the wavelength of the illumination light.

15. A defect inspection apparatus comprising:

an illumination device that irradiates a substrate to be inspected with illumination light, the substrate to be inspected including a resist layer having repetitive patterns formed on a top layer of the substrate; and an optical image forming system that forms an optical image of the substrate to be inspected according to light that emerges from the substrate to be inspected by the irradiation with the illumination light, wherein:

a wavelength of the illumination light is set so that intensity of the light from the surface of the substrate to be inspected, among the light that emerged from the substrate to be inspected, is greater than intensity of light that has passed through the surface of repetitive pattern layer formed below the resist layer.

* * * * *